(12) United States Patent
Kang et al.

(10) Patent No.: US 11,376,393 B2
(45) Date of Patent: Jul. 5, 2022

(54) DEVICE AND METHOD FOR TRAINING MEMORY USING BRAIN STIMULATION

(71) Applicants: THE ASAN FOUNDATION, Seoul (KR); UNIVERSITY OF ULSAN FOUNDATION FOR INDUSTRY COOPERATION, Ulsan (KR)

(72) Inventors: Dong Wha Kang, Seoul (KR); Dong Ho Kim, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 663 days.

(21) Appl. No.: 16/363,884

(22) Filed: Mar. 25, 2019

(65) Prior Publication Data
US 2019/0217046 A1    Jul. 18, 2019

Related U.S. Application Data

(63) Continuation of application No. PCT/KR2017/010631, filed on Sep. 26, 2017.

(30) Foreign Application Priority Data

Sep. 26, 2016 (KR) .................... 10-2016-0123203
Sep. 26, 2017 (KR) .................... 10-2017-0123892

(51) Int. Cl.
*A61M 21/00* (2006.01)
*A61B 3/113* (2006.01)
(Continued)

(52) U.S. Cl.
CPC ............ *A61M 21/00* (2013.01); *A61B 3/113* (2013.01); *A61B 5/162* (2013.01); *G16H 20/70* (2018.01);
(Continued)

(58) Field of Classification Search
CPC ............ A61M 21/00–02; A61B 5/163; A61B 5/16–18; A61B 3/113; G16H 20/70
See application file for complete search history.

(56) References Cited

U.S. PATENT DOCUMENTS 9,308,445 B1*  4/2016  Merzenich ............ A63F 13/537
2003/0073885 A1  4/2003  Theodoracopulos et al.
(Continued)

FOREIGN PATENT DOCUMENTS

KR       10-1114299 B1      3/2012
KR    10-2012-0046578 A     5/2012
(Continued)

OTHER PUBLICATIONS

The extended European search report issued by the European Patent Office dated Aug. 21, 2019, which corresponds to European Patent Application No. 17853504.3-1126 and is related to U.S. Appl. No. 16/363,884.
(Continued)

*Primary Examiner* — Thaddeus B Cox
(74) *Attorney, Agent, or Firm* — Studebaker & Brackett PC

(57) ABSTRACT

Disclosed are a device, a method, and a program for training memory using brain stimulation. The method includes at least: displaying a first problem on a task display portion of a screen; receiving a first response corresponding to the first problem; and evaluating a memory state of a user based on the first response. The first problem includes one or more output images to be displayed at a specific location within the task display portion, and the first response includes a result of comparing a previous first problem that was displayed before N times (N is a natural number) of executing the method, with the displayed first problem.

18 Claims, 4 Drawing Sheets

(51) Int. Cl.
  *A61B 5/16*   (2006.01)
  *G16H 20/70*  (2018.01)
  *G16H 50/30*  (2018.01)

(52) U.S. Cl.
  CPC ....... *G16H 50/30* (2018.01); *A61M 2021/005* (2013.01); *A61M 2205/3303* (2013.01); *A61M 2209/088* (2013.01); *A61M 2230/63* (2013.01)

(56) References Cited

U.S. PATENT DOCUMENTS

| | | | |
|---|---|---|---|
| 2004/0167380 A1 | 8/2004 | Simon | |
| 2007/0027406 A1* | 2/2007 | LaPlaca | A61B 5/4076 600/558 |
| 2014/0315169 A1* | 10/2014 | Bohbot | G06T 19/003 434/236 |
| 2015/0126899 A1* | 5/2015 | Ghajar | A61B 5/4064 600/558 |

FOREIGN PATENT DOCUMENTS

| | | |
|---|---|---|
| KR | 10-1297134 B1 | 8/2013 |
| KR | 10-1350957 B1 | 2/2014 |
| KR | 10-1564168 B1 | 10/2015 |
| WO | 2008/041346 A1 | 4/2008 |

OTHER PUBLICATIONS

International Search Report issued in PCT/KR2017/010631; dated Jan. 9, 2018.

\* cited by examiner

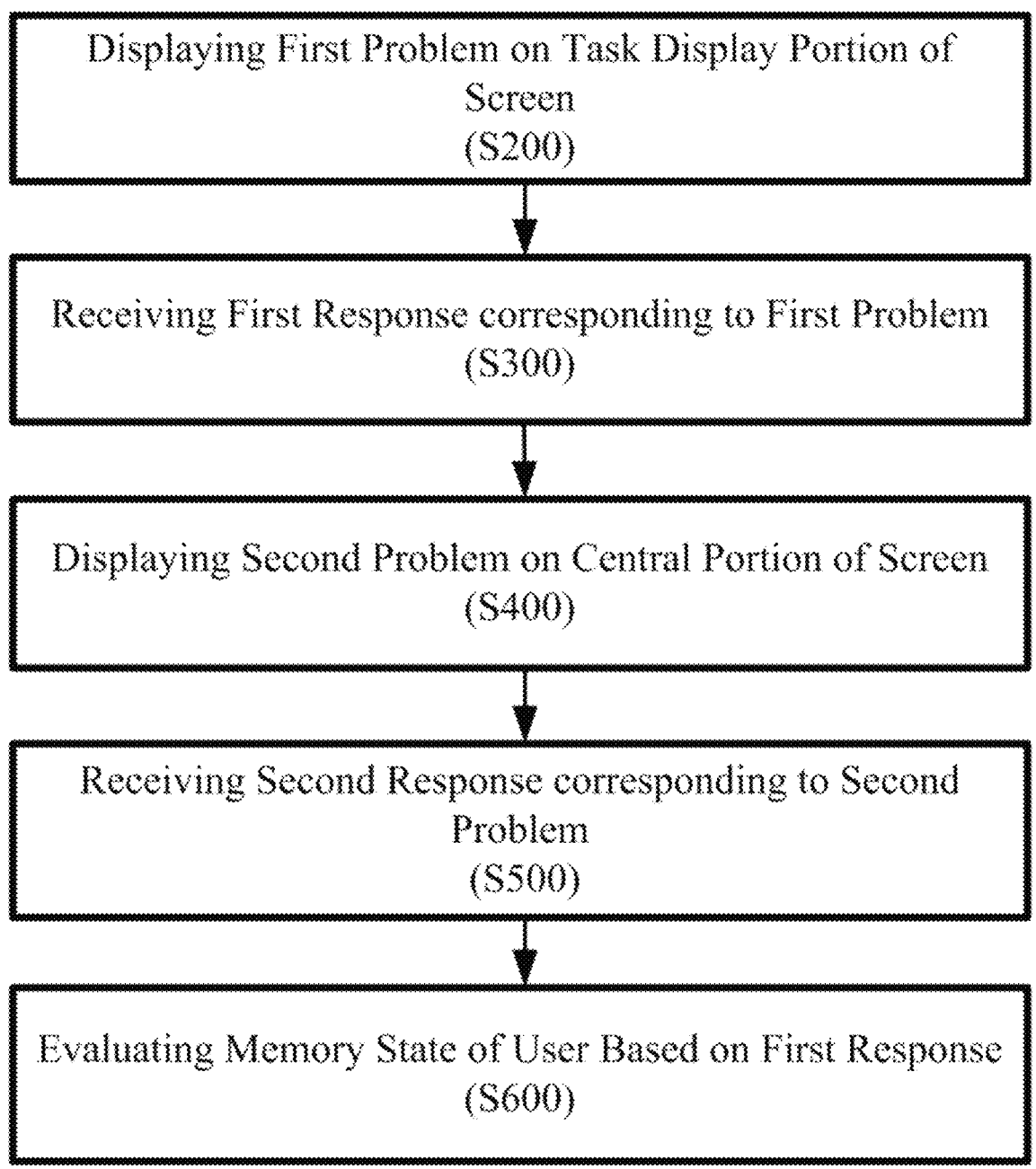

DEVICE AND METHOD FOR TRAINING MEMORY USING BRAIN STIMULATION

CROSS-REFERENCE TO RELATED APPLICATIONS

The present application is a continuation of International Patent Application No. PCT/KR2017/010631, filed Sep. 26, 2017, which is based upon and claims the benefit of priority to Korean Patent Application Nos. 10-2016-0123203, filed on Sep. 26, 2016, and 10-2017-0123892, filed on Sep. 26, 2017. The disclosures of the above-listed applications are hereby incorporated by reference herein in their entirety.

RELATED ART

Embodiments of the inventive concept described herein relate to a device and a method for training a memory, and more particularly, relate to a device and a method for stimulating brain to enhance memory. Embodiments of the inventive concept described also relates to a non-transitory computer-readable recording medium storing the above method.

For dementia patients due to brain damages or aging, they may have a problem with declining of spatial memory despite of not having a problem with visual perception. There is a visual perception training method for patients who have abnormal vision in a specific area because of damage to a specific part of the brain. However, a memory training method is required because there is no memory training method for dementia patients or older people with impaired spatial memory.

SUMMARY

Embodiments of the inventive concept provide a device and method for training spatial memory using brain stimulation, which enhances the spatial memory by simultaneously providing visual perception stimulation and spatial memory stimulation to a user's brain.

According to some embodiments, a method for memory training using brain stimulation includes displaying, by a processor, a first problem on a task display portion of a screen; receiving, by the processor, a first response corresponding to the first problem; and evaluating, by the processor, a memory state of a user based on the first response. The first problem includes one or more output images to be displayed at a specific location within the task display portion, and the first response includes a result of comparing a previous first problem that was displayed before N times (N is a natural number) of executing the method, with the displayed first problem.

According to some other embodiments, a memory training device using brain stimulation includes a processor configured to display a first problem on a task display portion, receive a first response corresponding to the first problem, and evaluate a memory state of a user based on the received first response. The first problem includes one or more output images to be displayed at a specific location within the task display portion, and the first response includes a result of comparing a previous first problem that was displayed before N times (N is a natural number) of executing a memory evaluation, with the displayed first problem.

BRIEF DESCRIPTION OF DRAWINGS

The above and other objects and features will become apparent from the following description with reference to the following figures, wherein like reference numerals refer to like parts throughout the various figures unless otherwise specified, and wherein:

FIG. 2 is a flowchart illustrating a memory training method using brain stimulation, according to some other embodiments of the present disclosure;

DETAILED DESCRIPTION

Figure 1:
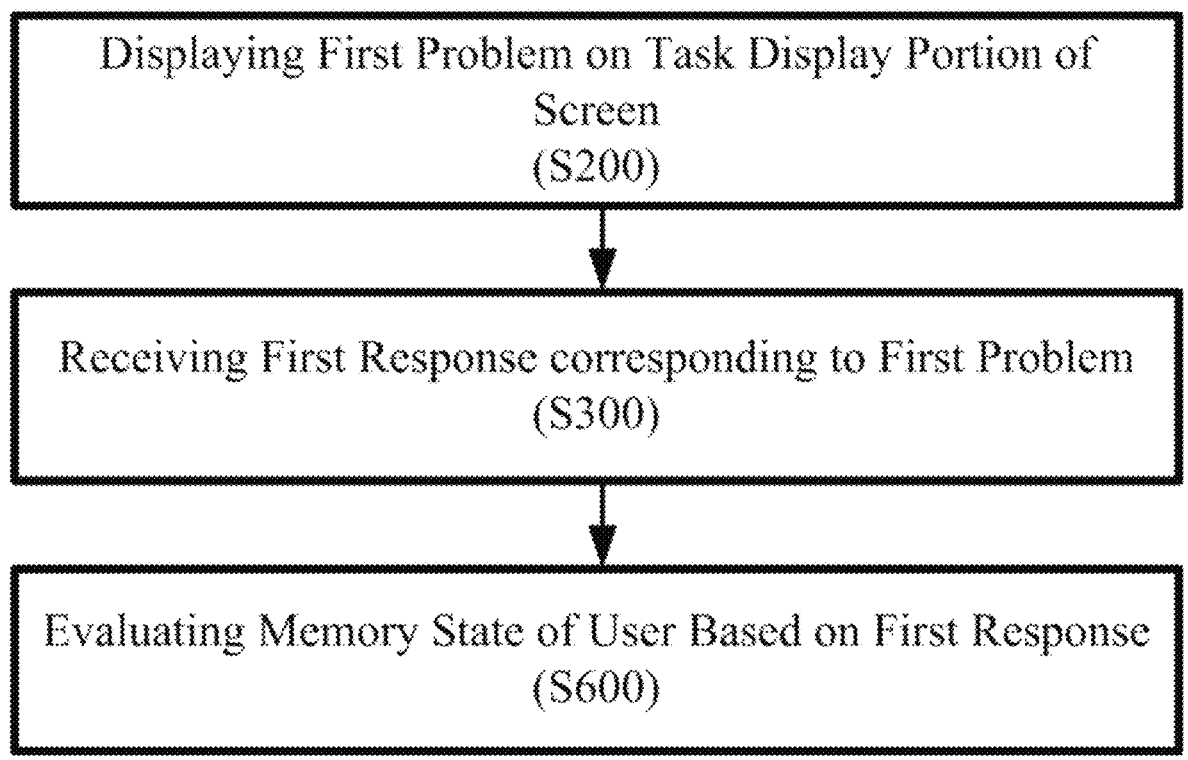
FIG. 1 is a flowchart illustrating a memory training method using brain stimulation, according to some embodiments of the present disclosure.

Hereinafter, exemplary embodiments of the inventive concept will be described in detail with reference to the accompanying drawings. The above and other aspects, features and advantages of embodiments of the present disclosure will become apparent from the following description of the following embodiments given in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept. The same reference numerals denote the same elements throughout the specification.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

In the present disclosure, a "processor" includes all the various devices capable of performing arithmetic processing. For example, the processor corresponds to not only a computer, such as a desktop personal computer (PC) or a notebook, but also a smart phone, a tablet PC, a cellular phone, a personal communication service phone (PCS phone), a mobile terminal of a synchronous/asynchronous International Mobile Telecommunication-2000 (IMT-2000), a palm PC, a personal digital assistant (PDA), and the like. Furthermore, in some examples, a processor corresponds to a server computer that receives information from a client device.

In the present disclosure, the "first problem" includes a problem that is displayed on a screen to provide memory training to a user. For example, the "first problem" is a problem that requires the user to determine whether the previous problem before N times (N is a natural number) is the same as the current problem.

In the present disclosure, the "first response" includes a response to the first problem, that is provided at a specific point in time.

In the present disclosure, the "second problem" includes a problem displayed to fix the user's gaze direction to a center of the screen. For example, the "second problem" is to display one of a plurality of objects (e.g., "ㄱ" or "ㅌ" (Korean letters), "A" or "B", or "⊟" or "⊜" (symbols)), which are distinguished on the center of the screen, on the center of the screen at the specific point in time.

In the present disclosure, the "second response" includes a response to the second problem, which is received from the user.

In the present disclosure, the "output image" includes an image displayed at a specific location on the screen by the first problem. For example, the "output image" includes a horizontal or vertical stripe image displayed within a specific quadrant on the screen.

In the present disclosure, the "screen image" is a screen itself on which one or more output images are arranged depending on the first problem. In some embodiments, the screen image is output to a general display device or output to a head-mounted display device. When the screen image is provided to the head-mounted display device, the screen image is generated as both a left-eye image and a right-eye image, in some embodiments.

In the present disclosure, the "central portion" includes a central area within the screen provided to the user, such as a central field of view.

In the present disclosure, the "peripheral portion" includes a remaining area other than the central portion of the screen, such as a peripheral field of view.

In the present disclosure, the "task display portion" includes an area where the output image being the task of memory training is provided within the screen provided to the user. In some embodiments, the "task display portion" corresponds to only the peripheral portion other than the central portion, or includes both the central portion and the peripheral portion.

Hereinafter, according to embodiments of the present disclosure, a device and a method for training memory using brain stimulation are described in detail with reference to the drawings.

FIG. 1 is a flowchart illustrating a memory training method using brain stimulation, according to some embodiments of the present disclosure.

Referring to FIG. 1, according to some embodiments of the present disclosure, a memory training method using brain stimulation includes an operation S200 (a step of displaying a first problem) of displaying a first problem on a task display portion of a screen, an operation S300 (a step of receiving a first response) of receiving a first response corresponding to the first problem, and an operation S600 (a step of evaluating the first response) of evaluating a memory state of the user based on the first response.

Hereinafter, the detailed description of each operation is provided.

In operation S200, the processor controls a screen to display a first problem on a task display portion of the screen. The first problem includes one or more output images to be displayed at a specific location within the task display portion. The first problem includes changing at least one of the number of output images, types of the output images, arrangement locations of the output images, and sizes of the output images, from a previous first problem.

In some embodiments, the first problem is variously provided by changing the arrangement locations of the output images included in the screen whenever the first problem is provided on the screen. For example, the processor generates another screen image by changing the location within the screen, at which the same output image is displayed. In some embodiments, to change the location of the output image is to change division areas in each of which the output image of the first problem is displayed or to change a point at which the output image is positioned within the same division area, when the task display portion is divided into a plurality of division areas.

Moreover, when generating the output image at various depths by implementing the task display portion in a three-dimensional (3D) space, the processor generates various types of problems by changing the depth at which the output image is displayed. For example, the processor displays the output image by dividing the output image into an area close to a reference depth (e.g., the depth at which the second problem is displayed when the second problem is provided) and an area far from the reference depth.

In particular, the operation S200 of displaying the first problem determines the location in the 3D space, in which the output image included in the first problem is displayed, based on the arrangement location in the 3D space of the second problem to be described later. In some embodiments, the perspective is formed in the 3D space based on a point at which images (i.e., a left-eye image and a right-eye image) provided to the left and right eyes forms convergence. Accordingly, while arranging the second problem to be described later at a specific depth, the processor performs convergence matching on a left-eye image and a right-eye image for the second problem; the processor implements a screen in which the output image is displayed at various depths based on the relative location of the second problem arranged at the reference depth by arranging the output image according to the first problem at a specific depth.

Furthermore, in some embodiments, the processor generates different first problems by changing the type (e.g., shape classification and character image classification) or the shape (e.g., horizontal and vertical stripe patterns) of an output image. For example, the processor generates a different problem by displaying the different shape of an output image (e.g., horizontal and vertical stripe patterns) at the same location of the task display portion.

Also, in some embodiments, the processor generates a different first problem by changing the size of the output image while the processor displays the type/shape of the same output image at the same location.

In operation S300, the processor receives the first response corresponding to the first problem (the operation of receiving the first response). In some embodiments, the first response is received from a user. The first response includes a result of comparing a previous first problem that was displayed before N times (N is a natural number), with the first problem currently displayed on the screen. For example, when N is 1, the processor receives the result of determining whether the immediately-preceding first problem (i.e., the screen image according to the immediately-preceding first problem) is the same as the current first problem (the screen image output to the current screen), as the first response. Moreover, for example, when N is not 1 but a specific natural number, the processor receives the result of comparing the screen image, which is provided at the trial before N times from the current trial, with the current screen image, from the user as the first response of the current trial.

In operation S600, the processor evaluates the memory state of the user based on the first response (the operation of evaluating the response). That is, when receiving the result of comparing to the screen image before N times, as the first response, the processor determines whether the stored screen image before N times is the same as the current screen image. To this end, when performing spatial memory training through the comparison to the trial before N times, the processor stores up to the screen image at the trial before N times. In addition, the processor deletes the screen image at the trial before N times after using the comparison between the screen image at the trial before N times and the screen image at the current trial. When it is determined that the first response entered from the user is correct, the processor promptly informs the user that the first response is correct and/or increases the cumulative number of correct answers.

Furthermore, in some embodiments, the processor determines the memory state of the user based on the number of correct answers and/or adjusts a level of difficulty of memory training. For example, when the memory training result at the user's specific N value is good, the processor increases the level of difficulty by increasing the N value of the memory training provided to the user at the next training. That is, in some embodiments, the processor increase the level of difficulty of the memory training by increasing a trial interval in which the user is required to remember the output image. Also, for example, the processor increases the level of difficulty by lowering the brightness or saturation of the output image displayed on the screen or by reducing the size of the output image.

In addition, in some embodiments, the processor adjusts the level of difficulty by adjusting the number of output images appearing in a screen image. As the number of output images increases, the level of difficulty increases because a layout between output images becomes complex. For example, when displaying a horizontal stripe and a vertical stripe as the output image, the processor generates a screen image by displaying a specific output image among the horizontal stripe or the vertical stripe, in a part of the division areas of the screen. Because the user needs to determine whether arrangement locations of the output images at the current trial are the same as those at the previous trial before N times, and whether the type of output image displayed at each location is the same as that at the previous trial before N times, the user receives the first problem of the high difficulty as compared with the case where a single output image is provided.

Furthermore, in some embodiments, the processor determines whether memory is degraded for any type of output image, based on the patient's memory training result. For example, depending on the patient's state, the memory is degraded for images displayed at specific locations within the screen, and the memory for specific shapes is degraded. Accordingly, in some embodiments, the processor grasps the type of the degraded memory of the patient, based on the brain stimulation training result. Furthermore, for the purpose of allowing the user to determine whether the screen images (i.e., the current screen image and the screen image before N times) with the difference of the specific trial interval are the same as each other, in some embodiments, the processor allows the user to visually and identically recognize the screen image provided based on the first problem of the same condition. To this end, in some embodiments, the processor applies various methods that allow the same screen image at each trial to be provided by the first problem of the same condition.

In some embodiments, the operation S200 of displaying the first problem includes measuring, by the processor, the gaze direction of the user and determining and providing the arrangement location of the output image according to the first problem based on the gaze direction. For example, in some embodiments, in the case where a user receives a screen image through a head-mounted display device, when the user moves his/her head or the direction of his/her eyeball in a state the user wears the head-mounted display device, the direction in which the user watches the same screen image is changed. Accordingly, in some embodiments, the processor obtains the gaze direction by recognizing the user's head movement or eye movement and determines the arrangement location of the output image based on the gaze direction.

Specifically, in some embodiments, the processor measures the head movement of the user, based on the head movement data obtained through the motion sensor included in the head-mounted display device. Moreover, the processor measures eye movement based on eye movement data obtained by an eye movement sensor (i.e., an eye-tracker) included in the head-mounted display device. Afterward, the processor calculates the gaze direction (i.e., the center direction of the screen) at a point in time when the user moves his/her head or eyeball. Afterward, the processor displays the output image based on the gaze direction (i.e., the center of the screen) to generate a screen image to be provided at a specific trial. That is, information about the arrangement location of the output image in the first problem is a relative location determined based on the gaze direction (i.e., the center direction of the screen), and the processor generates a screen image at each trial based on the information about the arrangement location of the output image in the first problem. As such, in some embodiments, the processor smoothly provides memory training even while the user is performing free head movement and eye movement.

In addition, in some embodiments, as illustrated in FIG. 2, the processor further includes an operation S400 of displaying a second problem in the central portion within a screen (a step of displaying the second problem) and an operation S500 of receiving the second response corresponding to the second problem (a step of receiving the second response). The second problem is to fix the user's gaze direction at a specific location. In some embodiments, the second problem is displayed simultaneously with the first problem displayed to one side of the task display portion. That is, in some embodiments, the processor provides a screen image for simultaneously displaying the first problem and the second problem on the screen such that the user identifies the first problem in the state where the user watches the central portion where the second problem is displayed. As the user watches the central portion in which the second problem is displayed to enter the correct answer for the second problem, the same condition that provides the screen image to the user's field of view is formed.

Also, when the second response to the second problem is not entered, the first response to the first problem is incorrect because it is determined that the gaze direction is not properly set to the center of the screen. As such, in some embodiments, the processor accurately generates the memory training result by excluding the first response entered in a state that is not suitable to answer to the first problem.

In addition, in some embodiments, the processor determines whether brain stimulation memory training is performed correctly in the state where the user's gaze is fixed to the center of the screen, based on the correct answer rate of the second problem displayed in the central portion. For example, when the user does not accurately watch the central portion where the second problem is displayed as the second problem is small in the middle of the screen, the processor determines whether the central fixation is correctly performed based on the correct answer rate of the second problem by setting a specific correct answer rate not to be exceeded. When the correct answer rate of the second response to the second problem is lower than a specific value, the processor determines that the training is not performed properly to provide a notification or to perform the training again.

Figure 3A:
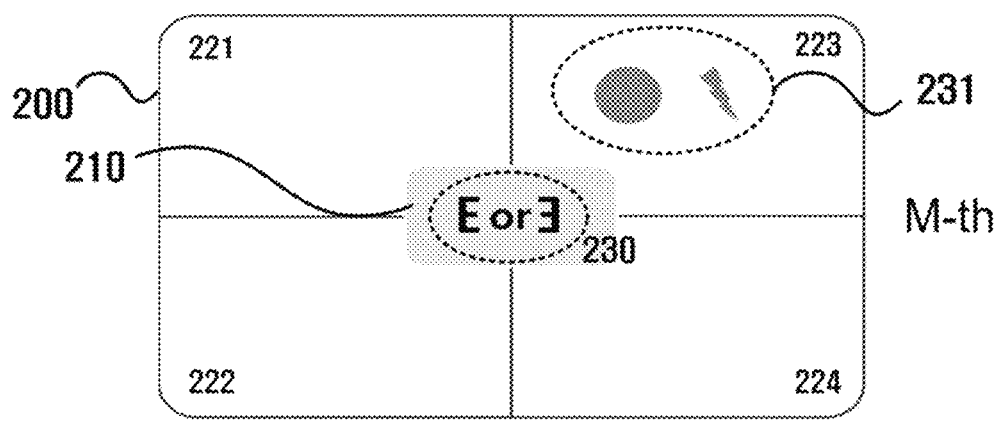
FIGS. 3A-3C are schematic diagrams illustrating a process of performing memory training by using a memory training method, according to some embodiments of the present disclosure.
Figure 3B:
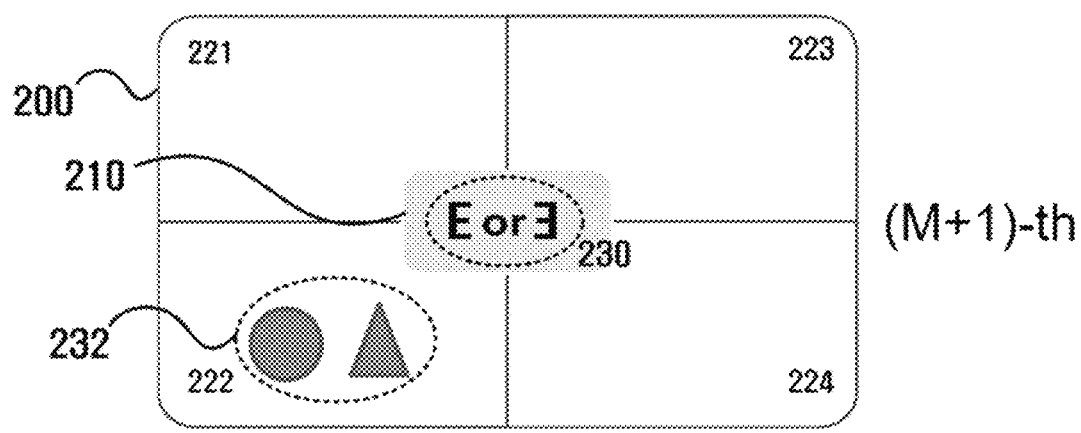
Figure 3C:
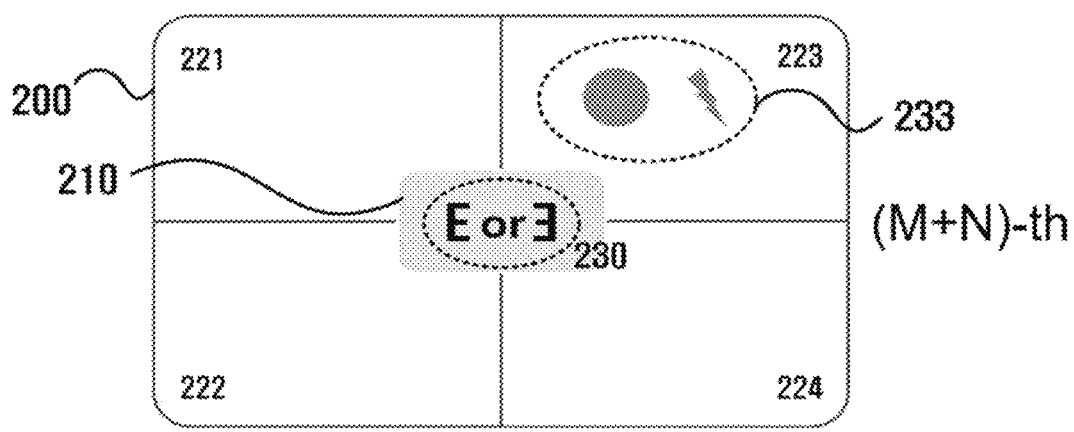

FIGS. 3A-3C are schematic diagrams illustrating a process of performing memory training by using a memory training method, according to some embodiments of the present disclosure. In particular, FIGS. 3A-3C describe a method for training memory based on a second problem in a state where a user's gaze direction is fixed at a center portion of a screen, according to some embodiments of the present disclosure.

Referring to FIG. 3A, the processor outputs a central portion 210, and task display portions 221, 222, 223 and 224 other than the central portion 210 as a memory training image 200.

The central portion 230 is the central area within a screen where a problem 230 for fixing a user's gaze direction is displayed. That is, in some embodiments, the central portion 210 includes a predetermined problem (i.e., a second problem) for fixing the user's focus to the center of the screen. For example, the central portion 210 includes a character or a figure that the user can guess, so that the user enters a response corresponding to the character or the figure included in the central portion 210.

The task display portions 221, 222, 223 and 224 are areas where an output image to be compared with an output image at a previous trial for the memory test of the user is provided. In some embodiments, the task display portion is divided into various ways or numbers. For example, at least one of quadrant task display portions 221, 222, 223 and 224 includes an output image according to the first problem the quadrants 221, 222, 223 and 224 are divided by intersecting a virtual horizontal line and a virtual vertical line with respect to the center. For example, the first problem included in the task display portion is associated with at least one of the spatial location, number, shape, and color of the output image (e.g., figure) displayed in at least one of quadrant task display portions 221, 222, 223 and 224. That is, the processor implements various screens (i.e., memory training images) by adjusting a quadrant location where the output image is provided, a location where the output image is displayed in quadrant, the type (e.g., a stripe or a character image) of the output image, the shape (e.g., the horizontal stripe or the vertical stripe) of output image, the number of output images.

Referring to FIG. 3A, the processor outputs a screen image 223 including the first problem 231 and the central portion 210, at the M-th view point as the M-th training image 200. Referring to FIG. 3B, the processor outputs the screen image including the second problem provided to the central portion 210 and a first problem 232 at the (M+1)-th view point provided to the task display portion 222, as the (M+1)-th training image 200. Referring to FIG. 3C, the processor outputs the screen image including the second problem provided to the central portion 210 and a first problem 233 at the (M+N)-th view point provided to the task display portion 223, as the (M+N)-th training image 200. In addition, in FIG. 3C, the processor receives the user's answer as to whether the first problem 233 included in the (M+N)-th training image 200 is the same as the first problem 231 included in the training image 200 before the M-th training image 200, through the user input unit 140. That is, the processor receives a response as to whether the screen image according to the first problem at the N-th view point is the same as the screen image according to the first problem at the (M+N)-th view point, from the user. For example, when the spatial location (e.g., a specific location in a specific quadrant), shape, number, size, color, or the like of the figure included in the first problem 233 included in the (M+N)-th training image 200 is the same as those of the first problem 231 included in the M-th training image 200, the user enters "O"; otherwise, the user enters "X".

Although omitted for convenience of description, in FIG. 3A, the user enters the answer as to whether the problem included in the image before the specific number of the M-th training image 200 is matched; in FIG. 3B, the user enters the answer as to whether the problem included in the image before the specific number of the (M+1)-th training image 200 is matched. As such, the user remembers the problem included in the task display portion of the training image before the specific number of times and improves short-term memory and mid- and long-term memory through repetitive training that compares the problem included in the task display portion of the training image before the specific number of times with the problem included in the task display portion of the current training image, thereby enhancing the spatial memory.

Through the inventive concept, the spatial memory rather than simple memory is enhanced through training. That is, the spatial memory is trained by allowing the user to remember the location of the output image provided in the screen image.

In particular, the hippocampus is responsible for the spatial memory of the brain, and only the visual perception training (i.e., training for providing patients with visual stimulation) stimulates the hippocampus by brain connectivity, thereby restoring the function. Accordingly, for the purpose of improving the hippocampus function responsible for spatial memory, the inventive concept provides the eye with repeatedly providing visual perception stimulation together with training to remind the space arrangement, thereby increasing the speed of spatial memory enhancement. That is, the inventive concept disclosed herein provides the spatial memory training to stimulate the hippocampus responsible for spatial-temporal memory, based on a brain area (e.g., primary visual area, parietal lobe, or frontal lobe) performing spatial-temporal egocentric (based on sensory receptors) processing and the brain connectivity of the hippocampus performing spatial-temporal allocentric processing (time space environment itself) and based on visual perception training providing the visual stimulation, thereby enhancing spatial memory.

Figure 4:
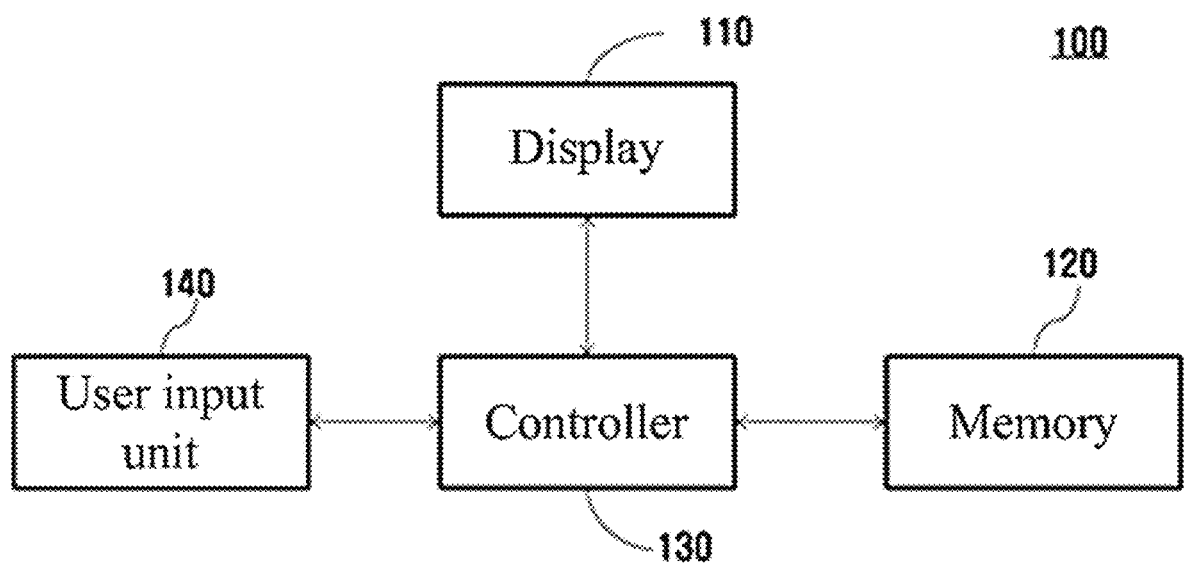
FIG. 4 is a schematic block diagram showing a configuration of a memory training device using brain stimulation, according to some embodiments of the present disclosure.

FIG. 4 is a schematic block diagram showing a configuration of a memory training device using brain stimulation, according to some embodiments of the present disclosure.

Referring to FIG. 4, a memory training device 100 includes all or part of a display 110, a memory 120, a controller 130, and a user input unit 140.

The memory training device 100 includes, but not limited to, a computer, a personal computer, a display device, a portable terminal, and the like. The memory training device 100 is a device for training spatial memory by visually stimulating the user's brain. Here, the spatial memory includes the memory of a spatial location, a shape, or the like of the visual mark (e.g., figure) appearing in front of the view field.

The memory 120 stores a memory training program. In some embodiments, the memory training program is a native program installed in advance in the memory training device 100 or is a program downloaded from an external server. In some embodiments, the memory 120 is an external memory connected to or inserted into the memory training device 100.

Further, the memory 120 may be implemented using any type or combination of suitable volatile and non-volatile memory or storage devices including hard disk, random access memory (RAM), static random access memory (SRAM), electrically erasable programmable read-only memory (EEPROM), erasable programmable read-only memory (EPROM), programmable read-only memory (PROM), read-only memory (ROM), magnetic memory, flash memory, magnetic or optical disk, multimedia card micro type memory, card-type memory (e.g., SD memory, XD memory, etc.), or other similar memory or data storage device.

When the memory training program is executed, the controller 130 outputs a training image corresponding to the visual perception training program to the display 110. In some embodiments, the training image includes a task display portion for fixing the user's focus to the center. In some embodiments, the task display portion includes a predetermined problem (i.e., first problem) for training the user's spatial memory. That is, the task display portion displays the output image according to the first problem, at a specific location in 2D or 3D space. In some embodiments, the task display portion uses only the peripheral portion or uses both the peripheral portion and the central portion.

The controller 130 may be implemented using any type or combination of suitable hardwares, such as one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a selective combination thereof.

Further, the display 110 may be implemented using known display technologies including, for example, a liquid crystal display (LCD), a thin film transistor-liquid crystal display (TFT-LCD), an organic light-emitting diode display (OLED), a flexible display and a three-dimensional display. The memory training device 100 may include one or more of such displays.

In some embodiments, the first problem is performed on the task display portion in various manners. For example, the output image (e.g., figure) of the first problem is displayed in a specific quadrant of four quadrants of the task display portion, and at least one of the arrangement location in the specific quadrant, the shape of an output image, the size of the output image, and the color of the output image is adjusted.

In some embodiments, the user input unit 140 receives a user input associated with a memory training image. In some embodiments, the user enters a response corresponding to the problem included in the central portion and the problem included in the task display portion, through the user input unit 140.

The user input unit 140 generates input data responsive to user manipulation of an associated input device or devices. Examples of such devices include a keypad, a dome switch, a touchpad (e.g., static pressure/capacitance), a jog wheel, a jog switch, etc.

In some embodiments, the controller 130 outputs the central portion and the task display portion including the first problem, to the display 110 as an M-th training image; the controller 130 outputs the central portion and the task display portion including the second problem, to the display 110 as the (M+N)-th training image; the controller 130 receives the user's answer as to whether the second problem included in the (M+N)-th training image is the same as the first problem included in the training image before N times, via the user input unit 140. That is, the controller 130 receives the first response, which is a result of comparing the first problem provided before N times with the first problem currently provided, from the user via the user input unit 140 to determine whether the first response is correct.

Moreover, in some embodiments, the controller 130 adjusts the level of difficulty of the problem included in the task display portion, based on the correct answer rate of the answer entered via the user input unit 140. For example, the level of difficulty of a problem in the task display portion is adjusted by adjusting the number of N or by adjusting at least one of the number, the shape, and the color of the figure displayed in the task display portion.

Furthermore, in some embodiments, the controller 130 provides a second problem for fixing the user's gaze direction to the center of the screen in the central portion of the display 110. The second problem is a predetermined problem for focusing the user's attention such that the user's focus is fixed to the center. When providing the second problem to the central portion, the controller 130 only uses the peripheral portion as a task display portion providing the first problem such that the first problem does not overlap with the second problem.

According to some embodiments of the present disclosure, the memory training method using brain stimulation may be implemented as a program (or application) to be executed in combination with a hardware computer and may be stored in media.

According to some embodiments of the present disclosure, the memory training program using brain stimulation may be directly installed in a device (i.e., a device with a display unit) outputting a screen or may be installed in a device connected to a display device. For example, when providing a memory training image via a head-mounted display device, the memory training program may be installed in a mobile terminal (e.g., a smartphone or a PC) to which the head-mounted display device is connected, and the memory training program using brain stimulation may be installed in the head-mounted display device having a processor capable of arithmetic processing.

The above-described program may include a code encoded by using a computer language such as C, C++, JAVA, a machine language, or the like, which a processor (i.e., CPU) can read through the device interface of the computer, such that the computer reads the program and performs the methods implemented with the program. The code may include a functional codes associated with the function that defines functions necessary to perform the methods, and may include a control code associated with an execution procedure necessary for the processor of the computer to perform the functions in a predetermined procedure. Furthermore, the code may further include additional information necessary for the processor of the computer to perform the functions or a memory reference-related code associated with the location (address) of the internal or external memory of the computer, at which the media needs to be checked. Moreover, when the processor of the computer needs to communicate with any other remote computer or any other remote server to perform the functions, the code may further include a communication-related code associated with how to communicate with any other remote computer or server using the communication module of the computer, what information or media should be transmitted or received during communication, or the like.

The storing media may mean the media that does not store data for a short period of time such as a register, a cache, a memory, or the like but semi-permanently stores to be read by the device. Specifically, for example, the storing media include, but are not limited to, ROM, RAM, CD-ROM, magnetic tape, floppy disk, optical data storage device, and the like. That is, the program may be stored in various recording media on various servers that the computer can access, or various recording media on the computer of the user. In addition, the media may be distributed to a computer system connected to a network, and a computer-readable code may be stored in a distribution manner.

Further, in the embodiments described above, a method for memory training using brain stimulation is considered as using displaying a problem, receiving a response, and evaluating a memory state in a specific manner that sufficiently limits the use of the displaying, receiving, and evaluating concepts to the practical application of memory training.

Although some embodiments of the present disclosure have been described herein with reference to accompanying drawings, it should be understood by those skilled in the art that the inventive concept may be embodied in other specific forms without departing from the spirit or essential features thereof. Therefore, it should be understood that the above embodiments are not limiting, but illustrative.

According to some embodiments of the present disclosure, the spatial memory may be enhanced by simultaneously providing visual perception stimulation and spatial memory stimulation to a user's brain. In particular, when the spatial memory deteriorates due to brain damage or aging (e.g., dementia patients) or when the spatial memory is poor because a person does not grow normally, the spatial memory may be enhanced through brain stimulation. Moreover, growing children may enhance their spatial memory by simultaneously applying visual perception stimulation and spatial memory stimulation.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for memory training using brain stimulation, the method comprising:
    displaying, by a processor, a first problem on a task display portion of a screen, wherein the first problem comprises one or more output images to be displayed at a specific location within the task display portion;
    receiving, by the processor, a first response corresponding to the first problem, wherein the first response comprises a result of comparing a previous first problem that was displayed N times before (N is a natural number) of executing the method, with the displayed first problem; and
    evaluating, by the processor, a memory state of a user based on the first response,
    wherein the displaying the first problem comprises:
    measuring, by the processor, a gaze direction of the user;
    determining an arrangement location or arrangement locations of the one or more output images to be displayed as the first problem, based on the gaze direction; and
    displaying the first problem according to the determined arrangement locations.

2. The method of claim 1, further comprising:
    displaying, by the processor, a second problem on a central portion of the screen; and
    receiving a second response corresponding to the second problem.

3. The method of claim 2, wherein the displaying the first problem comprises:
    determining a location in a three-dimensional space including the one or more output images of the first problem, based on an arrangement location of the second problem displayed in the three-dimensional space.

4. The method of claim 3, wherein the screen is a screen of a head-mounted display device.

5. The method of claim 2, wherein the screen is a screen of a head-mounted display device.

6. The method of claim 1, wherein the first problem is displayed by changing, from the previous first problem, at least one of the number of the one or more output images, a type or types of the one or more output images, the arrangement location or arrangement locations of the one or more output images, and a size or sizes of the one or more output images, and
    wherein the first response includes information on the user's interpretation whether a screen image including the displayed first problem is the same as a previous screen image including the previous first problem.

7. The method of claim 6, wherein the screen is a screen of a head-mounted display device.

8. The method of claim 1, further comprising:
    adjusting a value of the N, depending on the memory state of the user.

9. The method of claim 8, wherein the adjusting comprises
    increasing the value of the N when the evaluated memory state is higher than a predetermined threshold state.

10. The method of claim 8, wherein the screen is a screen of a head-mounted display device.

11. The method of claim 1, further comprising:
    lowering brightness or saturation of the one or more output images displayed on the screen or by reducing a size or sizes of the one or more output images displayed on the screen, when the evaluated memory state is higher than a predetermined threshold state.

12. The method of claim 1, further comprising:
    increasing the number of the one or more output images displayed on the screen when the evaluated memory state is higher than a predetermined threshold state.

13. The method of claim 1, wherein the screen is a screen of a head-mounted display device.

14. The method of claim 1, wherein the screen is a screen of a head-mounted display device.

15. The method of claim 14, wherein the measuring the gaze direction comprises
    measuring a head movement of the user, based on head movement data obtained through a motion sensor included in the head-mounted display device; and
    determining the gaze direction of the user based on the measured head movement.

16. The method of claim 14, wherein the measuring the gaze direction comprises measuring eye movement based on eye movement data obtained by an eye movement sensor included in the head-mounted display device; and determining the gaze direction of the user based on the measured eye movement.

17. A non-transitory computer-readable recording medium storing a memory training program using brain stimulation, the program configured to be performed by a processor coupled to a computer hardware, and including instructions to execute the method of claim 1.

18. A memory training device using brain stimulation, the device comprising a processor configured to:

display a first problem on a task display portion;

receive a first response corresponding to the first problem; and evaluate a memory state of a user based on the received first response, wherein the first problem comprises one or more output images to be displayed at a specific location within the task display portion, wherein the first response comprises a result of comparing a previous first problem that was displayed N times before (N is a natural number) of executing a memory evaluation, with the displayed first problem, and wherein the processor is further configured to:

measure a gaze direction of the user;

determine an arrangement location or arrangement locations of the one or more output images to be displayed as the first problem, based on the gaze direction; and display the first problem according to the determined arrangement locations.

* * * * *